(12) United States Patent
Jadhav et al.

(10) Patent No.: US 7,951,390 B2
(45) Date of Patent: *May 31, 2011

(54) SLOW-RELEASE MICROCAPSULE COMPOSITION FOR SAFE DELIVERY OF AGRICULTURALLY ACTIVE MATERIAL

(75) Inventors: Prakash Mahadev Jadhav, Mumbai (IN); Jaidev Rajnikant Shroff, Mumbai (IN); Shirsat Rajan Ramakant, Mumbai (IN); Ahire Dnyaneshwar Laxman, Ankleshwar (IN)

(73) Assignee: United Phosphorus, Ltd., Mumbai (IN)

( * ) Notice: Subject to any disclaimer, the term of this patent is extended or adjusted under 35 U.S.C. 154(b) by 1188 days.

This patent is subject to a terminal disclaimer.

(21) Appl. No.: 11/617,370

(22) Filed: Dec. 28, 2006

(65) Prior Publication Data

US 2007/0196410 A1  Aug. 23, 2007

Related U.S. Application Data

(63) Continuation-in-part of application No. 11/168,994, filed on Jun. 29, 2005, now Pat. No. 7,229,949.

(60) Provisional application No. 60/583,616, filed on Jun. 30, 2004.

(51) Int. Cl.
*A01N 25/34* (2006.01)
*A61K 9/50* (2006.01)

(52) U.S. Cl. .................. 424/408; 424/493

(58) Field of Classification Search .......... 504/359; 424/418, 493
See application file for complete search history.

(56) References Cited

U.S. PATENT DOCUMENTS

| | | | |
|---|---|---|---|
| 4,285,720 | A | 8/1981 | Scher |
| 4,956,129 | A | 9/1990 | Scher et al. |
| 5,160,529 | A | 11/1992 | Scher et al. |
| 5,741,521 | A | 4/1998 | Knight et al. |
| 5,846,554 | A | 12/1998 | Scher et al. |
| 5,993,842 | A | 11/1999 | Scher et al. |
| 6,015,571 | A | 1/2000 | Scher et al. |
| 6,113,935 | A | 9/2000 | Rodson et al. |
| 6,113,936 | A | 9/2000 | Takebayashi et al. |
| 6,133,197 | A | 10/2000 | Chen et al. |
| 6,149,843 | A | 11/2000 | Scher et al. |
| 6,358,520 | B1 | 3/2002 | Lo et al. |
| 6,419,942 | B1 | 7/2002 | Lo et al. |
| 6,514,439 | B2 | 2/2003 | VanKoppenhagen et al. |
| 6,554,540 | B1 | 4/2003 | Corsan |
| 6,955,823 | B2 | 10/2005 | Casson et al. |
| 7,229,949 | B2 * | 6/2007 | Jadhav et al. ............... 504/359 |
| 2002/0044968 | A1 | 4/2002 | van Lengerich |

FOREIGN PATENT DOCUMENTS

EP  1101527 A1  5/2001

* cited by examiner

*Primary Examiner* — Alton N Pryor
(74) *Attorney, Agent, or Firm* — Yancy IP Law, PLLC

(57) ABSTRACT

A slow-release microcapsule composition for the safe delivery of agriculturally active material is formed using an encapsulation process. A microencapsulated suspension of agriculturally active material includes an encapsulating agent formed from a graft copolymer of starch and at least on vinyl monomer.

32 Claims, No Drawings

SLOW-RELEASE MICROCAPSULE COMPOSITION FOR SAFE DELIVERY OF AGRICULTURALLY ACTIVE MATERIAL

CROSS-REFERENCE TO RELATED APPLICATION

This application is a continuation-in-part of pending U.S. application Ser. No. 11/168,994 filed on Jun. 29, 2005, which claims the benefit of Provisional Application No. 60/583,616 filed on Jun. 30, 2004, both of which are incorporated fully herein by reference.

BACKGROUND OF THE INVENTION

1. Field of the Invention

The present invention relates to slow-release microcapsules containing biologically active compounds. Particularly, the present invention relates to a slow-release microcapsule composition for safe delivery of agriculturally active material and a process for preparing the same.

2. Description of the Related Art

Insecticides, particularly pyrethroids such as lambda cyhalothrin, cypermethrin, fenvalerate, permethrin, alpha-cypermethrin, and similar compounds, which are moderately toxic in the technical form, have a high skin irritant property and in some cases may provoke an adverse skin reaction such as burning, tingling, numbness or prickling sensation, also generally known as paraesthesia. These skin irritant properties are most pronounced in the areas of an operator's face, hand, and neck during application of these insecticides. For delivering such agriculturally active materials to a target, encapsulation or microencapsulation is one of the safest modes. Encapsulation, or more specifically microencapsulation, is increasingly being used to target specific insects, as it also provides a safer handling of toxic fungicides and insecticides. A microcapsule is a $10^{-3}$ m to $10^{-9}$ m diameter particle, composed of an inner core material and an outer shell.

Microencapsulation of a number of different agriculturally active materials and pesticides has been known for many years by using various processes or techniques for solving other problems such as volatility, UV degradation of the actives, reducing aquatic toxicity, pollution in air, water, soil, and also protecting untargeted insects and the like.

The use of microcapsules for the slow or controlled release of liquid or solid active ingredient is well known in the art. Typically, for slow or controlled release, the walls of the microcapsules are porous in nature releasing the entrapped material to the surrounding medium at a slow or controlled rate by diffusion through the pores of the wall. The controlled-release techniques have improved the efficiency of herbicides, insecticides, bactericides and fertilizers.

Non-agricultural uses of slow-release or controlled release microcapsules include encapsulated dyes, pigments, inks, flavoring agents, fragrances etc.

Typically, microcapsules may be formed by physical methods such as spray coating, spray drying, pan coating, rotary disk atomization and the like; and chemical methods such as phase separation, interfacial polymerization, simple and complex coacervation method and the like. The prior art includes microcapsules produced by interfacial polymerization by forming a capsular wall that involves hydrolysis of an isocyanate monomer to form an amine which in turn reacts with another isocyanate monomer to form the polyurea enclosure polymers by reaction of isocyanate monomers. Capsules capable of controlled release of encapsulated organic active material enclosed in a polyurea capsule are also described.

Generally, release rates of the microcapsules are governed by the capsule particle size, the thickness of the wall and the permeability of the wall. It is also known that release rates can be appreciably varied by altering the chemical composition and thus the permeability of microcapsule walls. For example, the prior art describes microcapsules formed from an aminoplast shell wall and an encapsulated ingredient enclosed within the wall containing a base-cleavable ester moiety. In the presence of base, the capsule walls relatively quickly disintegrate or degrade so as to produce a relatively quick release of the encapsulated materials. If the capsules are not in a basic environment, they function as typical diffusion controlled release microcapsules, permitting release of the encapsulated substance into the surrounding area in a controlled manner which is determined primarily by wall characteristics of the shells such as thickness, capsule size, permeability, etc. If, on the other hand, the capsules are placed in a basic environment, preferably in a situation in which the resulting pH is from about 8 to about 13, preferably from about 9 to about 11, the cross-linking moieties in the capsule wall are cleaved so as to "trigger" or initiate breakdown of the capsule wall. Depending on the conditions of the environment and on the particular structure of the capsule wall, the resulting breakdown may occur relatively quickly or relatively slowly. Additionally, the prior art provides acid-triggered or -sensitive microcapsules which contain encapsulated material that are sensitive to the presence of acid, and on exposure to an acidic environment break down and/or become porous so as to release the encapsulated substance into the surrounding environment. Furthermore, the prior art also describes microcapsule wall compositions containing disulfide units and providing a semi-permeable barrier. The walls are made from materials where the wall forming materials contain sulfur atoms such as polythiol compounds.

The prior arts known for the encapsulation include a polyurea shell wall or urea/formaldehyde shell. However, the capsule shell wall materials are not biodegradable and may not be environmental friendly. Moreover, the isocyanates may cause skin/eye irritation due to its high toxicity.

The co-pending application U.S. Ser. No. 11/168,994 provides a safe delivery system of agriculturally active material is formed using an encapsulation process. A microencapsulated suspension of agriculturally active material includes an encapsulating agent formed from a graft copolymer of starch and at least one vinyl monomer. The polymers used in the encapsulation process as described in the co-pending application are biodegradable polymer. Starch is hydrophilic and a partially water soluble polymer. In the encapsulation process, the starch provides a polymeric outer shell to an inner core material after grafting with the vinyl monomer. Furthermore, the microcapsules of agriculturally active material were produced without using any diisocyanate/isocyanate as a shell material. The microcapsules described in the co-pending application are preferably more suitable for the quick or fast release of the active material and is more suitable for foliar application.

Slow-release microcapsules provide longer term efficacy as the encapsulated material release the active ingredient over a period of time. Moreover, slow-release microcapsules containing the agriculturally active ingredients may be useful in agricultural and non-agricultural applications.

SUMMARY OF THE INVENTION

The present invention relates to a microcapsule composition for safe delivery of agriculturally active material that is preferably a slow-release composition. According to a preferred embodiment of the present invention, a slow-release microcapsule for safe delivery of an agriculturally active material having an inner core including an agriculturally active material; an outer shell including a graft copolymer having a starch and at least one vinyl monomer and having a core to polymer ratio of 1:10 to 10:1 is provided. The starch and vinyl monomer is preferably present in a ratio is 1:5 to 5:1, preferably, 1:4 to 4:1, more preferably, 1:3 to 4:1. According to the invention, the microcapsules have a size of 5 to 500 microns, preferably 5 to 300 microns and more preferably 5 to 100 microns. The core of the slow-release microcapsule includes the active material, such as an insecticide, preferably a pyrethroid, more preferably lambda cyhalothrin.

Another embodiment of the present invention provides an encapsulation process for preparing a slow-release microencapsulated suspension for a safe delivery system of an agriculturally active material, comprising the steps of: a) preparing an organic phase comprising an agriculturally active water immiscible material and a solvent, in the presence of at least one surfactant; b) preparing an aqueous phase comprising water, a starch, and a protective colloid; c) heating the aqueous phase to obtain a gelatinized aqueous phase followed by cooling; d) adding the organic phase of step (a) into the gelatinized aqueous phase of step (c) under low shear to form an oil-in-water emulsion; e) adding an initiator maintaining an acidic pH to the oil-in-water emulsion of step (d) in an inert atmosphere; f) adding a vinyl monomer for graft reaction to occur and resulting in obtaining a microencapsulated suspension; g) neutralizing the microencapsulated suspension of step (f) followed by adding a structuring agent.

The microcapsule of the present invention provide a slow-release of the active material at a controlled rate. Furthermore, the slow-release microcapsules may be designed with the required amount of active material suitable for slow-release agricultural and non-agricultural applications. Moreover, the slow-release microcapsules containing the agriculturally active material may be useful in agricultural and non-agricultural applications.

DETAILED DESCRIPTION OF THE INVENTION

The present invention provides slow-release composition for safe delivery of an agriculturally active material, preferably by microencapsulation. The agriculturally active material is preferably a pyrethroid, most preferably lambda cyhalothrin. However, the encapsulated material may be a combination of two or more such agriculturally active material.

It has been found that the release rates of the microcapsule comprising starch and vinyl monomer may be slowed or delayed by increasing the size of the microcapsule. This may be accomplished either by increasing the size of the core of microcapsule and/or by increasing the thickness of polymeric shell wall made of starch and vinyl monomer. However, if the size of core of the microcapsule is only increased, it may result in formation of a variable core size with variable wall thickness of the polymeric shell that may result in relatively slow-release when compared to the fast release microcapsule, but the release rates may be variable. Therefore, it may not be suitable for providing a slow-release microcapsules for non-agricultural purposes, particularly for public health uses. Similarly, if only the wall thickness is increased, capacity reduction of the active may occur. Furthermore, residual concentration of the shell material may also exist. Also, larger size of microcapsules may not remain as suspension.

It was surprisingly found that the microcapsules produced by increasing the quantity of core to polymeric shell ratio in the range of 1:10 to 10:1 and also increasing the thickness of the microcapsule shell wall by providing the starch to vinyl monomer in the ratio of 1:5 to 5:1, preferably 1:4 to 4:1, more preferably 1:3 to 4:1 provide a slow-release of the active at a controlled rate. Furthermore, the slow-release microcapsules may be designed with the required amount of active material suitable for slow-release agricultural and non-agricultural applications.

Accordingly, an aspect of this invention includes a microcapsule having an inner core having an agriculturally active material; an outer shell including a graft copolymer comprising a starch and at least one vinyl monomer having a core to polymeric shell ratio of 1:10 to 10:1. The microcapsule of the present invention has a size range of 5 to 500 microns. Preferably, the microcapsule of the present invention has a size range of 5 to 300 microns, more preferably 5 to 100 microns to remain in the suspension. It should be understood by the person skilled in the art, the size of the microcapsules of the present invention may be varied from 5 to 500 microns to suit the formulation and mode of delivery of the formulation.

The outer shell including graft copolymer having starch and vinyl monomer are preferably present in a ratio of 1:5 to 5:1, preferably 1:4 to 4:1, more preferably 1:3 to 4:1. This ratio of starch and vinyl monomer increases the wall thickness of the microcapsule of the present invention. It has to be understood that the starch to vinyl monomer ratio may be varied depending upon the size of the core and the quantity of active in the core to form a thick wall in order to delay the release of the active.

The active materials suitable to be delivered using the slow-release microcapsule of the present invention include, by are not limited to, insecticides such as lambda cyhalothrin, cypermethrin, fenvalerate, permethrin, alpha-cypermethrin, and similar compounds which are moderately toxic in the technical form, have a high skin irritant property and in some cases may provoke an adverse skin reaction such as burning, tingling, numbness or prickling sensation, also generally known as paraesthesia.

According to a preferred embodiment of the present invention, the active material is a pyrethroid, preferably lambda Cyhalothrin. The microcapsule of the present invention may preferably include lambda Cyhalothrin in the range of 0.1 to 25%

The material used for the microcapsule outer shell is a starch grafted with at least one vinyl monomer, which provides a biodegradable microcapsule shell material. A vinyl monomer is defined herein to include a monomer with at least one vinyl group. The ratio between the starch and the vinyl monomer is 1:5 to 5:1 and preferably the ratio is 1:4 to 4:1 and more preferably is 1:3 to 4:1

The preferred starch is a hydrophobic and partially water soluble polymer, which is used as a polymer outer shell to an inner core material after grafting with the vinyl monomer. The starch used is preferably starch from corn, wheat, potatoes, rice, sago and sorghum. Additionally, the starch may include suitable starch derivatives, preferably starch ethers, starch esters, cross-link starch, grafted starch and oxidized starch.

The vinyl monomer used to produce a starch graft polymer is preferably any monomer polymerizable on the thinned gelatinized starch through a free radical initiator. The vinyl monomer or combination of vinyl monomers can be chosen such that starch graft co-polymers particles are dispersed in an aqueous continuous phase. The preferred vinyl monomers include, but are not limited to, vinyl halide, vinyl ethers, alkyl vinyl ketones, N-Vinyl carbzole, N-Vinyl pyrolidone, Vinyl pyrridine, styrene, alkyl styrene and the like. When single vinyl monomers are used to form the graft polymer, the preferred vinyl monomer preferably includes, but is not limited to, acrylonitrile, methyl methacrylate, vinyl acetate, 2-ethyl hexyl acrylate and the lower alkyl acrylates such as methyl acrylates, ethyl acrylate, and n-butyl acrylates.

The surfactant system in combination with the low shear increases the microcapsule size. It is well known in the art that the increase in microcapsule size delays the release of active material from the microcapsule.

The surfactant is preferably an anionic or non-ionic surfactant with HLB range about 12-16 that is high enough to form stable oil/water emulsion. Suitable surfactants include, but are not limited to, polyethylene glycol ethers of linear alcohol, ethoxylated nonyl-phenol, naphthalene sulphonates, salts of long chain alkyl benzene sulphonate, block-co-polymers of propylene oxide and ethylene oxide, and anionic/nonionic blends.

The microcapsule of the present invention may include a protective colloid, further surfactant(s), and other excipients including dispersing agents, structuring agents, and the like.

The release rates of the active material from the microcapsule of the present invention, preferably, lambda Cyhalothrin are from 24 hours to 20 hours for 50% active content release after application/use.

The present invention may further include an absorbent or adsorbent such as for example silica, kaolin clay, zeoloite, bentonite, applugite, bolomite, and the like alone or in combination thereof to further slow down the release of the active.

Another aspect of the invention includes an encapsulation process for preparing a slow-release microencapsulated suspension for a safe delivery system of an agriculturally active material, comprising the steps of: a) preparing an organic phase comprising an agriculturally active water immiscible material and a solvent, in the presence of at least one surfactant; b) preparing an aqueous phase comprising water, a starch, and a protective colloid; c) heating the aqueous phase to obtain a gelatinized aqueous phase followed by cooling; d) adding the organic phase of step (a) into the gelatinized aqueous phase of step (c) to form an oil-in-water emulsion under low shear e) adding an initiator maintaining acidic pH to the oil-in-water emulsion of step (d) in an inert atmosphere; f) adding a vinyl monomer for graft reaction to occur and resulting in obtaining a microencapsulated suspension; g) neutralizing the microencapsulated suspension of step (f) followed by adding a structuring agent.

The surfactant system in combination with the low shear increases the microcapsule size. It is well known in the art that the increase in microcapsule size delays the release of active material from the microcapsule.

The organic phase is preferably added into the gelatinized aqueous phase slowly with high shear to form an oil-in-water emulsion having oil droplet with a preferred size of 5 to 500 microns; preferably 5 to 300 microns, more preferably 5 to 100 microns. Free radical initiator is preferably added into this oil-in-water emulsion and stirred while an inert gas, preferably $N_2$, was purged to keep the process oxygen-free.

The process was preferably maintained at a temperature range of 22-55° C. and at a preferred pH maintained at 2.0-5.0 preferably with the help of concentrated $HNO_3$.

Vinyl monomer was preferably added at a constant rate such that a grafting reaction occurs at the interface of the organic phase and gelatinized aqueous phase, while maintaining the process at a preferred temperature range of 15-30° C. and a microencapsulated suspension is formed. The microencapsulated suspension is then neutralized, preferably Xanthan gum was added to the microencapsulated suspension. The microencapsulated suspension was preferably stirred for an additional 30-60 minutes to produce microcapsules having a preferred oil droplet size 5 to 500 microns.

The process according to the present invention wherein the core to polymer shell is present in a ratio is 1:10 to 10:1

The active materials suitable to be delivered using the slow-release microcapsule of the present invention preferably includes insecticides such as lambda cyhalothrin, cypermethrin, fenvalerate, permethrin, alpha-cypermethrin, and similar compounds which are moderately toxic in the technical form, have a high skin irritant property and in some cases may provoke an adverse skin reaction such as burning, tingling, numbness or prickling sensation, also generally known as paraesthesia.

The active material preferred is pyrethroid, more particularly lambda cyhalothirn. According to the preferred embodiment, lambda Cyhalothrin is present in the range of 0.1 to 25% to suit the slow-release applications in both agricultural and non-agricultural applications.

The material used for the microcapsule outer shell is a starch grafted with at least one vinyl monomer, which provides a biodegradable microcapsule shell material. A vinyl monomer is defined herein to include a monomer with at least one vinyl group. The preferred ratio between the starch and the vinyl monomer is 1:5 to 5:1 and preferably the ratio is 1:4 to 4:1 and more preferably is 1:3 to 4:1.

The preferred starch is a hydrophilic and partially water soluble polymer, which is used as a polymer outer shell to an inner core material after grafting with the vinyl monomer. The starch used is preferably starch from corn, wheat, potatoes, rice, sago and sorghum. Additionally, the starch may include suitable starch derivatives, preferably starch ethers, starch esters, cross-link starch and oxidized starch.

The vinyl monomer used to produce a starch graft polymer is preferably any monomer polymerizable on the thinned gelatinized starch through a free radical initiator. The vinyl monomer or combination of vinyl monomers is preferably chosen such that starch graft co-polymers particles are dispersed in an aqueous continuous phase. The preferred vinyl monomers include, but are not limited to, vinyl halide, vinyl ethers, alkyl vinyl ketones, N-Vinyl carbzole, N-Vinyl pyrolidone, Vinyl pyrridine, styrene, alkyl styrene and the like. When single vinyl monomers are used to form the graft polymer, the preferred vinyl monomer preferably includes, but is not limited to acrylonitrile, methyl methacrylate, vinyl acetate, 2-ethyl hexyl acrylate and the lower alkyl acrylates such as methyl acrylates, ethyl acrylate, and n-butyl acrylates.

The surfactant is preferably an anionic or non-ionic surfactant with HLB range about 12-16 that is high enough to form stable oil/water emulsion. Suitable surfactants include, but are not limited to, polyethylene glycol ethers of linear alcohol, ethoxylated nonyl-phenol, naphthalene sulphonates, salts of long chain alkyl benzene sulphonate, block-co-polymers of propylene oxide and ethylene oxide, and anionic/nonionic blends.

Suitable solvents include, but are not limited to, alkyl benzene, methylnapthalene, alkyl esters of pthalic acid, trimellitic acid, aromatic hydrocarban such as xylene, naphthalene mix of aromatics aliphatic or cycloaliphatic hydrocarbon such as hexane, heptane, phthalates, ketones such as cyclohexanone or acetophenone or chlorinated hydrocarbons, vegetable oils or mix of such two or more solvents.

The free radical initiator is any polymerization initiator which acts to initiate free radical polymerization on gelatinized thinned starch to the substantial exclusion of initiation of homo or co-polymerization of the monomer or mixture of monomer utilized to form starch graft co-polymer is suitable initiator. Ceric ammonium nitrate is an example of such initiator. Another preferred initiation is the combination of hydrogen peroxide and acetate ion.

The protective colloid can be selected from a wide range of materials which must have the property of absorbing on the surface of oil droplets. The suitable colloid includes, but is not limited to, one or more methyl cellulose, polyvinyl alcohol, poly-acrylamide, poly(methyl vinyl ether/maliec anhydride), graft co-polymers, alkali metals and alkaline earth metals of alkyl naphthalene sulphonate. Preferably, however, the protective colloid is selected from alkali metals and alkaline earth metals of alkyl naphthalene sulphonate.

Antifreezing agent may be used to make the formulation workable in any atmosphere. Antifreezing agent may include, but are not limited to, ethylene glycol, diethylene glycol, propylene glycol, glycerol etc The biocide is preferably methyl paraban, ethyl paraban, formaldehyde, glutaraldehyde, 2-bromo-2-nitropropane-1,3 diol, 4,4 dimethyloxazolide, 7-ethybicyclo oxazolide and others. The neutralizing agent is preferably an organic aliphatic amine such as tri-ethanol amine.

The structuring agent is preferably selected from xanthan gum, guar gum, arabic gum, HPMC, CMC and others.

EXAMPLES

The following are non-limiting examples, illustrating the present encapsulation process and safe delivery system.

Example 1

| 1) Organic phase | |
| --- | --- |
| Lambda Cyhalothrin (Purity 95%) | 52.63 g |
| Solvesso-200 | 52.00 g |
| Calcium salt of alkyl benzene sulfonic acid | 05.00 g |
| Polyoxyethylene Styrineted Phenol Ethoxylate | 05.00 g |
| 2) Aqueous Phase | |
| Starch | 10.00 g |
| PEG | 25.00 g |
| Geropon TA 72 | 10.00 g |
| Emulsol 101 | 50.00 g |
| Methyl paraban | 5.00 g |
| Xanthan gum (2% gel) | 20.00 g |
| Vinyl acetate | 10.00 g |
| Ceric ammonium nitrate (10% in 1 Normal HNO3) | 20.00 g |
| Triethanol amine | 2.50 g |
| Water | QS |
| Total | 500.00 g |

The above composition can be prepared be the process of encapsulation as below:

1. The organic phase was prepared by mixing 52.63 g of lambda cyhalothrin technical in 52.00 g Solvesso-200 along with 5.00 g of the calcium salt of alkyl benzene sulfonic acid (anionic surfactant) and 05.00 g of Polyoxyethylene styrineted phenol (nonionic surfactant) by continuously stirring—to get a clear solution;

2. The aqueous phase was prepared by dissolving 10.00 g of Geropon TA-72 and 25.00 g of PEG along with 50.00 g Emulsol-101 and 10.00 g Starch in water and this was heated to 70-90° C. to form a gelatinized aqueous phase, which was cooled to 15-30° C.;

3. The organic phase was added into the gelatinized aqueous phase slowly with high shear to form an oil-in-water emulsion having oil droplet with a size less than 10 microns and 20.00 g free radical initiator was added into this oil-in-water emulsion and stirred while an inert gas nitrogen was purged to keep the process oxygen-free.

The process was maintained at a temperature range of 30 to 55° C. and at a pH maintained at 2 to 4 with the help of concentrated nitric acid.

Thereafter 10 g of vinyl acetate monomer was added at a constant rate such that a grafting reaction occurs at the interface of the organic phase and gelatinized aqueous phase, while maintaining the process at a temperature range of 20-55° C. and a microencapsulated suspension is formed.

After the grafting reaction was completed, the microencapsulated suspension was neutralized with 2.50 g of triethanaolamine.

Thereafter, 20.00 g of Xanthan gum (2% gel) was added to the microencapsulated suspension.

The microencapsulated suspension was stirred for an additional 30-60 minutes to produce microcapsules of lambda cyhalothrin having an oil droplet size less 10 microns.

TABLE 1

Release Rates of the Composition of Example 1

| Capsule Size | RPM/ time of string | Conc. Surfactant | Total content | % Free Content | % Release 15 min | % Release 30 Min | % release 24 hr |
|---|---|---|---|---|---|---|---|
| 10 microns | 500/10 min | 02.00 | 11.19 | Nil | 12.00 | 21.00 | 50.00 |

Example 2

1) Organic phase

| | |
|---|---|
| Lambda Cyhalothrin (Purity 95%) | 52.63 g |
| Solvesso-200 | 52.00 g |
| Calcium salt of alkyl benzene sulfonic acid | 3.00 g |
| Polyoxyethylene Styrineted Phenol Ethoxylate | 3.00 g |

2) Aqueous Phase

| | |
|---|---|
| Starch | 10.00 g |
| PEG | 25.00 g |
| Geropon TA 72 | 10.00 g |
| Emulsol 101 | 50.00 g |
| Methyl paraban | 5.00 g |
| Xanthan gum (2% gel) | 20.00 g |
| Vinyl acetate | 10.00 g |
| Ceric ammonium nitrate (10% in 1 Normal HNO3) | 20.00 g |
| Triethanol amine | 2.50 g |
| Water | QS |
| Total | 500.00 g |

The above composition can be prepared by following the process as described in Example-1 except keeping the capsule size 20 microns and pH 3.2 (adjusted by using concentrated nitric acid after initiator was added).

TABLE 2

Release Rates of Example 2

| Capsule Size | RPM/ time of string | % Conc. Surfactant | Total content | % Free Content | % Release 15 min | % Release 30 Min | % release 24 hr |
|---|---|---|---|---|---|---|---|
| 20 microns | 100/10 min | 1.20 | 11.86 | 0.28 | 09.00 | 15.00 | 30.00 |

Example 3

1) Organic phase

| | |
|---|---|
| Lambda Cyhalothrin (Purity 95%) | 52.63 g |
| Solvesso-200 | 52.00 g |
| Calcium salt of alkyl benzene sulfonic acid | 1.500 g |
| Polyoxyethylene Styrineted Phenol Ethoxylate | 1.500 g |

2) Aqueous Phase

| | |
|---|---|
| Starch | 10.00 g |
| PEG | 25.00 g |
| Geropon TA 72 | 10.00 g |
| Emulsol 101 | 50.00 g |
| Methyl paraban | 5.00 g |
| Xanthan gum (2% gel) | 20.00 g |
| Vinyl acetate | 10.00 g |
| Ceric ammonium nitrate (10% in 1 Normal HNO3) | 20.00 g |
| Triethanol amine | 2.50 g |
| Water | QS |
| Total | 500.00 g |

The above composition can be prepared by following the process as described in Example-1 except keeping the capsule size 40 microns and pH 3.2 (adjusted by using concentrated nitric acid after initiator was added).

TABLE 3

Release Rates of Composition of Example 3

| Capsule Size | RPM/ time of string | % Conc. Surfactant | Total content | % Free Content | % Release 15 min | % Release 30 Min | % release 24 hr |
|---|---|---|---|---|---|---|---|
| 40 microns | 60/10 min | 0.60 | 12.05 | 0.75 | 06.38 | 08.38 | 13.85 |

Example 4

1) Organic phase

| | |
|---|---|
| Lambda Cyhalothrin (Purity 95%) | 52.63 g |
| Solvesso-200 | 52.00 g |
| Calcium salt of alkyl benzene sulfonic acid | 1.00 g |
| Polyoxyethylene Styrineted Phenol Ethoxylate | 1.00 g |

2) Aqueous Phase

| | |
|---|---|
| Starch | 10.00 g |
| PEG | 25.00 g |
| Geropon TA 72 | 10.00 g |
| Emulsol 101 | 50.00 g |
| Methyl paraban | 5.00 g |
| Xanthan gum (2% gel) | 20.00 g |
| Vinyl acetate | 10.00 g |
| Ceric ammonium nitrate (10% in 1 Normal HNO3) | 20.00 g |
| Triethanol amine | 2.50 g |
| Water | QS |
| Total | 500.00 g |

The above composition can be prepared by following the process as described in Example-1 except keeping the capsule size 60 microns and pH 3.8 (adjusted by using concentrated nitric acid after initiator was added).

TABLE 4

Release rates of Composition of Example 4

| Capsule Size | RPM/ time of string | % Conc. Surfactant | Total content | % Free Content | % Release 15 min | % Release 30 Min | % release 24 hr |
|---|---|---|---|---|---|---|---|
| 60 microns | 30/10 min | 0.400 | 11.75 | 0.86 | 4.85 | 6.95 | 10.00 |

The following examples are processed and analyzed in a same manner as from examples 1 to 4.

Example-5

1) Organic phase

| | |
|---|---|
| Lambda Cyhalothrin (Purity 95%) | 52.63 g |
| Solvesso-200 | 52.00 g |
| Calcium salt of alkyl benzene sulfonic acid | 1.00 g |
| Polyoxyethylene Styrineted Phenol Ethoxylate | 1.00 g |

2) Aqueous Phase

| | |
|---|---|
| Starch | 10.00 g |
| PEG | 25.00 g |
| Geropon TA 72 | 10.00 g |
| Emulsol 101 | 50.00 g |
| Methyl paraban | 5.00 g |
| Xanthan gum (2% gel) | 20.00 g |
| Vinyl acetate | 50.00 g |
| Ceric ammonium nitrate (10% in 1 Normal HNO3) | 20.00 g |
| Triethanol amine | 2.50 g |
| Water | QS |
| Total | 500.00 g |

TABLE 5

Fast Release Rates Of The Microencapsulated Suspension Of the Co-Pending Application 11/168,994

| Capsule Size | RPM/ time of string | % Conc. Surfactant | Total content | % Free Content | % Release 15 min | % Release 30 Min | % release 24 hr |
|---|---|---|---|---|---|---|---|
| 3.5 microns | 1500–2000 | −02.00 | 12.00 | 0.58 | 59.9 | 62.33 | 82.30 |

Example-6

1) Organic phase

| | |
|---|---|
| Lambda Cyhalothrin (Purity 95%) | 27.00 g |
| Solvesso-200 | 20.00 g |
| Calcium salt of alkyl benzene sulfonic acid | 0.500 g |
| Polyoxyethylene Styrineted Phenol Ethoxylate | 1.00 g |

2) Aqueous Phase

| | |
|---|---|
| Starch | 50.00 g |
| PEG | 25.00 g |
| Geropon TA 72 | 10.00 g |
| Emulsol 101 | 50.00 g |
| Methyl paraban | 5.00 g |
| Xanthan gum (2% gel) | 10.00 g |
| Vinyl acetate | 10.00 g |
| Ceric ammonium nitrate (10% in 1 Normal HNO3) | 30.00 g |
| Triethanol amine | 2.50 g |
| Water | QS |
| Total | 500.00 g |

Example-7

1) Organic phase

| | |
|---|---|
| Lambda Cyhalothrin (Purity 95%) | 52.63 g |
| Solvesso-200 | 52.00 g |
| Calcium salt of alkyl benzene sulfonic acid | 1.00 g |
| Polyoxyethylene Styrineted Phenol Ethoxylate | 1.00 g |

2) Aqueous Phase

| | |
|---|---|
| Starch | 30.00 g |
| PEG | 25.00 g |
| Geropon TA 72 | 10.00 g |
| Emulsol 101 | 50.00 g |
| Methyl paraban | 5.00 g |
| Xanthan gum (2% gel) | 20.00 g |
| Vinyl acetate | 10.00 g |
| Ceric ammonium nitrate (10% in 1 Normal HNO3) | 20.00 g |
| Triethanol amine | 2.50 g |
| Water | QS |
| Total | 500.00 g |

Example-8

1) Organic phase

| | |
|---|---|
| Lambda Cyhalothrin (Purity 95%) | 105.50 g |
| Solvesso-200 | 80.00 g |
| Calcium salt of alkyl benzene sulfonic acid | 5.00 g |
| Polyoxyethylene Styrineted Phenol Ethoxylate | 5.00 g |

2) Aqueous Phase

| | |
|---|---|
| Starch | 20.00 g |
| PEG | 25.00 g |
| Geropon TA 72 | 10.00 g |
| Emulsol 101 | 50.00 g |
| Methyl paraban | 5.00 g |
| Xanthan gum (2% gel) | 18.00 g |
| Vinyl acetate | 10.00 g |
| Ceric ammonium nitrate (10% in 1 Normal HNO3) | 25.00 g |
| Triethanol amine | 2.50 g |
| Water | QS |
| Total | 500.00 g |

Although the present invention has been disclosed in terms of a preferred embodiment, it will be understood that numerous additional modifications and variations could be made thereto without departing from the scope of the invention as defined by the following claims:

The invention claimed is:

1. A slow-release microcapsule for safe delivery of an agriculturally active material comprising,
   (a) an inner core including an agriculturally active material;
   (b) an outer shell including a graft copolymer comprising a starch and at least one vinyl monomer and having a core to polymer shell ratio of 1:10 to 10:1.

2. The slow-release microcapsule of claim 1 wherein the starch and the vinyl monomer are present in a ratio is 1:5 to 5:1.

3. The slow-release microcapsule of claim 1 wherein the microcapsule have a size of 5 to 500 microns.

4. The slow-release microcapsule of claim 1 wherein the agriculturally active material is a pyrethroid.

5. The slow-release microcapsule of claim 4 wherein the pyrethroid is lambda Cyhalothrin.

6. The slow-release microcapsule of claim 1 wherein the vinyl monomer is selected from the group consisting of vinyl acetate, vinyl halide, vinyl ethers, alkyl vinyl ketones, N-Vinyl carbzole, N-Vinyl pyrolidone, Vinyl pyrridine, styrene, alkyl styrene, and acrylic acid.

7. The slow-release microcapsule of claim 1 wherein the starch is selected from the group consisting of potato, oat, wheat, sorghum, rice, corn, and combinations thereof.

8. An encapsulation process for preparing a slow-release microencapsulated suspension for a safe delivery system of an agriculturally active material, comprising the steps of:
   a) preparing an organic phase comprising an agriculturally active water immiscible material and a solvent, in the presence of at least one surfactant;
   b) preparing an aqueous phase comprising water, a starch, and a protective colloid;
   c) heating the aqueous phase to obtain a gelatinized aqueous phase followed by cooling;
   d) adding the organic phase of step (a) into the gelatinized aqueous phase of step (c) under low shear to form an oil-in-water emulsion;
   e) adding an initiator by maintaining an acidic pH to the oil-in-water emulsion of step (d) in an inert atmosphere;
   f) adding a vinyl monomer for graft reaction to occur and resulting in obtaining a microencapsulated suspension; and
   g) neutralizing the microencapsulated suspension of step (f) followed by adding a structuring agent.

9. The encapsulation process of claim 8, wherein the vinyl monomer is selected from the group consisting of vinyl halide, vinyl ethers, alkyl vinyl ketones, N-vinyl carbzole, N-Vinyl pyrolidone, vinyl pyrridine, styrene, alkyl styrene, vinyledenehalides, itaconic acid, and 1,3-butadine.

10. The encapsulation process of claim 8 wherein the starch is selected from the group consisting of potato, oat, wheat, sorghum, rice and combinations thereof.

11. The encapsulation process of claim 8, wherein the starch and the vinyl monomer are present in a ratio of 1:5 to 5:1.

12. The encapsulation process of claim 8, wherein said initiator is a free radical initiator.

13. The encapsulation process of claim 8, wherein said initiator is ceric ammonium nitrate.

14. The encapsulation process of claim 8, wherein said surfactant is an anionic surfactant or a non-ionic surfactant or a combination thereof.

15. The encapsulation process of claim 8, wherein said step of preparing an aqueous phase further comprises a biocide.

16. The encapsulation process of claim 15, wherein said biocide is selected from the group consisting of methyl paraban, ethyl paraban and butyl paraban.

17. The encapsulation process of claim 8, wherein said step of preparing an aqueous phase further comprises a dispersant.

18. The encapsulation process of claim 17, wherein said dispersant is selected from the group consisting of Emulsol 101, Soprophor FL, Soprophor FLK and combinations thereof.

19. The encapsulation process of claim 8, wherein said protective colloid is an alkyl metal or an alkaline earth metals of alkyl naphthalene sulphonate.

20. The encapsulation process of claim 8, wherein said agriculturally active water immiscible material is a pyrethroid.

21. The encapsulation process of claim 8, wherein said agriculturally active water immiscible material is Lambda Cyhalothrin.

22. The encapsulation process of claim 8, wherein said step of preparing an aqueous phase further comprises a second surfactant.

23. The encapsulation process of claim 8, wherein said step of preparing an aqueous phase further comprises an anti-freezing agent.

24. The encapsulation process of claim 8, wherein said step of heating said aqueous phase includes heating at a temperature of 65-85° C.

25. The encapsulation process of claim 8, wherein the structuring agent is selected from the group consisting of xanthan gum, guar gum, and arabic gum.

26. The encapsulation process of claim 8, wherein said step of adding an initiator to the oil-in-water emulsion includes maintaining a pH between 2-5.

27. The encapsulation process of claim 8, wherein said step of adding an initiator to the oil-in-water emulsion includes maintaining a temperature ranging between 15-30° C.

28. The encapsulation process of claim 8, wherein said step of adding vinyl monomer includes maintaining a temperature of 15-30° C.

29. The encapsulation process of claim 8, wherein said step of neutralizing the microencapsulated suspension includes neutralizing with an organic aliphatic amine.

30. The encapsulation process of claim 8, wherein said step of preparing an organic phase includes continuously stirring to get a clear solution.

31. The encapsulation process of claim 8, wherein said step of heating the aqueous phase is followed by cooling to a temperature of 20-45° C.

32. The encapsulation process of claim 8, wherein said inert atmosphere is an oxygen-free inert atmosphere.

* * * * *